(12) United States Patent
Stein et al.

(10) Patent No.: US 10,786,285 B2
(45) Date of Patent: Sep. 29, 2020

(54) PARAXIAL REVISION ROD-TO-ROD CONNECTOR

(71) Applicant: Stryker European Holdings I, LLC, Kalamazoo, MI (US)

(72) Inventors: Joshua Stein, Hoboken, NJ (US); Carla Bandeira, Voorhees, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 176 days.

(21) Appl. No.: 15/606,279

(22) Filed: May 26, 2017

(65) Prior Publication Data

US 2017/0348026 A1 Dec. 7, 2017

Related U.S. Application Data

(60) Provisional application No. 62/346,078, filed on Jun. 6, 2016.

(51) Int. Cl.
*A61B 17/70* (2006.01)
*A61B 17/64* (2006.01)

(52) U.S. Cl.
CPC ........ *A61B 17/7049* (2013.01); *A61B 17/705* (2013.01); *A61B 17/7043* (2013.01); *A61B 17/645* (2013.01); *A61B 17/7041* (2013.01); *A61B 17/7052* (2013.01)

(58) Field of Classification Search
CPC .... A61B 17/701; A61B 17/7032–7046; A61B 17/7049; A61B 17/705; A61B 17/7052; A61B 17/8605–866
See application file for complete search history.

(56) References Cited

U.S. PATENT DOCUMENTS

| 5,810,815 | A | 9/1998 | Morales |
| 6,187,005 | B1 * | 2/2001 | Brace .............................. 606/61 |
| 6,280,445 | B1 | 8/2001 | Morrison et al. |
| 6,485,491 | B1 | 11/2002 | Farris et al. |
| 7,976,567 | B2 | 7/2011 | Null et al. |
| 8,016,861 | B2 | 9/2011 | Mitchell et al. |

(Continued)

FOREIGN PATENT DOCUMENTS

DE 102012202749 A1 8/2013

OTHER PUBLICATIONS

Partial European Search Report for EP 17 18 1196 completed Dec. 8, 2017.

(Continued)

*Primary Examiner* — Tessa M Matthews
(74) *Attorney, Agent, or Firm* — Lerner, David, Littenberg, Krumholz & Mentlik, LLP

(57) ABSTRACT

Disclosed herein are an orthopedic rod-to-rod connector and rod-to-rod connector assemblies for spinal fusion surgery. The rod-to-rod connector may include a first connector portion and a second connector portion. The first connector portion may have a first aperture configured to receive at least a portion of a bone-engaging screw and a first spinal rod. The second connector portion may be rotatably connected with the first connector portion and may include a second aperture to receive a second spinal rod. The second connector portion may be L-shaped and may include a set screw to control rotation of the first connector portion with respect to the second connector portion.

17 Claims, 9 Drawing Sheets

(56) References Cited

U.S. PATENT DOCUMENTS

| | | | |
|---|---|---|---|
| 8,337,532 B1 | 12/2012 | McLean et al. | |
| 8,523,906 B2 | 9/2013 | McLean et al. | |
| 8,882,803 B2 | 11/2014 | Iott et al. | |
| 8,906,067 B2 | 12/2014 | Traynelis et al. | |
| 8,998,961 B1 | 4/2015 | Ziemek et al. | |
| 9,247,964 B1 * | 2/2016 | Shoshtaev | A61B 17/70 |
| 2005/0010215 A1 | 1/2005 | Delecrin et al. | |
| 2007/0225708 A1 | 9/2007 | Biedermann et al. | |
| 2007/0250061 A1 | 10/2007 | Chin et al. | |
| 2007/0270836 A1 | 11/2007 | Bruneau et al. | |
| 2009/0036929 A1 | 2/2009 | Reglos et al. | |
| 2011/0004251 A1 | 1/2011 | Sweeney et al. | |
| 2011/0046675 A1 | 2/2011 | Barrus et al. | |
| 2013/0006306 A1 | 1/2013 | Saidha et al. | |
| 2014/0135840 A1 | 5/2014 | McClintock et al. | |
| 2014/0249584 A1 | 9/2014 | Seex | |
| 2014/0277156 A1 | 9/2014 | Hammer | |
| 2015/0223844 A1 | 8/2015 | Leff et al. | |
| 2016/0058478 A1 * | 3/2016 | Agarwal | A61B 17/7049 |
| 2017/0238969 A1 | 8/2017 | Sylvia et al. | |
| 2017/0265901 A1 * | 9/2017 | Hawkins | A61B 17/7035 |
| 2018/0132905 A1 * | 5/2018 | Le Couedic | A61B 17/7053 |
| 2018/0228516 A1 * | 8/2018 | Armstrong | A61B 17/705 |
| 2018/0228518 A1 * | 8/2018 | Carruth | A61B 17/7049 |

OTHER PUBLICATIONS

European Search Report for EP 17174582 completed on Nov. 2, 2017.
Extended European Search Report for EP17181196 dated Mar. 23, 2018.

* cited by examiner

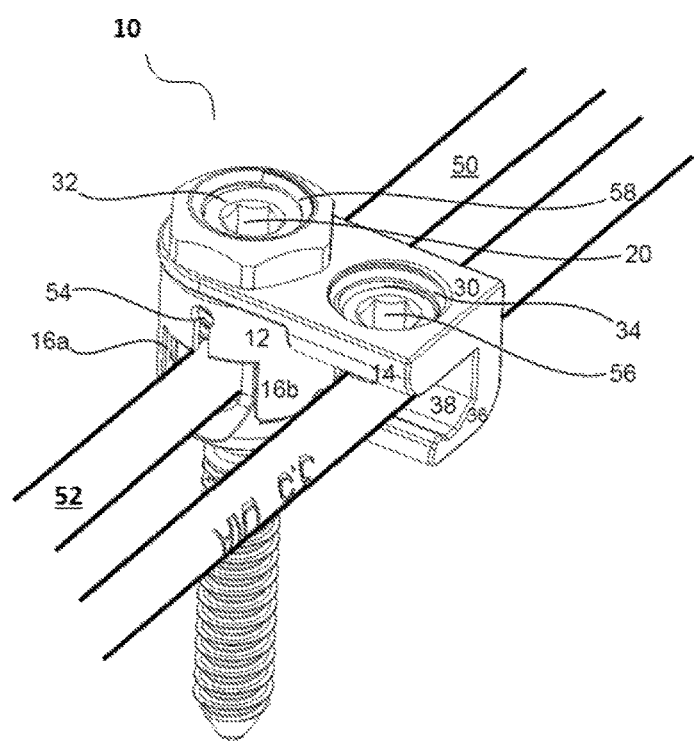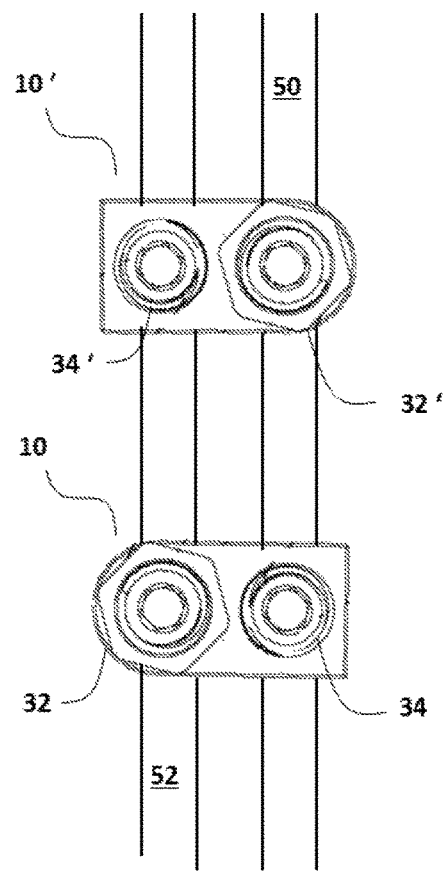
FIG. 11A
FIG. 11B

PARAXIAL REVISION ROD-TO-ROD CONNECTOR

CROSS-REFERENCE TO RELATED APPLICATION

The present application claims the benefit of the filling date of U.S. Provisional Patent Application No. 62/346,078, filed Jun. 6, 2016, the disclosure of which is hereby incorporated herein by reference.

BACKGROUND OF THE INVENTION

The present invention relates to spinal fusion surgery involving the use of pedicle (or lateral mass screws in the case of the cervical spine), and in particular, to devices and methods for adding additional spinal rod segments to already placed pedicle or lateral mass screw and rod constructs.

The spinal column is a complex system of bones and connective tissues that provides support for the body and protects the spinal cord. The system includes a number of vertebrae arranged to form a strong pillar-like structure, with each vertebral body cushioned by intervertebral discs placed between adjacent bodies. These discs are formed from a fibro-cartilage material and not only protect the spinal column from compressive forces, but also allow for movement of the vertebral bodies with respect to each other.

Many spinal disorders result from the degeneration of the spinal discs and/or misalignment of the vertebral bodies. Spinal fixation is a technique often used to correct such disorders by fusing together one or more levels of vertebral bodies. For instance, pedicle or lateral mass screws are inserted in different vertebral bodies and linked together via spinal rods. This acts to immobilize the involved vertebral bodies and may be coupled with the introduction of materials or implants that cause the vertebral bodies to grow together.

However, at a later point, it may be necessary to fuse additional vertebral bodies, especially in adjacent levels that may be negatively impacted by the initial fusion or otherwise subject of similar maladies as the original level. Typically, these revision procedures involve removing already implanted spinal rods, implanting additional pedicle or lateral mass screws and linking together all of the implanted pedicle or lateral mass screws with a new rod. Such a procedure takes time and removal of previously implanted rods may be rather difficult. Furthermore, it may be that vertebral bodies at a different regions of the spine (e.g., cervical, thoracic or lumbar) may require fusion together. Given the differing size of the vertebral bodies at these levels, it may be required to utilize differently sized and configured pedicle or lateral mass screws, which in turn may make it difficult to link the screws with a single spinal rod.

Therefore, there exists a need for improved devices and methods that allow for easier pedicle or lateral mass screw revision surgery and/or allow for multiple regions of the spine to be fused utilizing pedicle or lateral mass screws.

BRIEF SUMMARY OF THE INVENTION

The present invention is directed to a rod-to-rod connector that is useful in, inter alia, connecting two differently sized spinal rods together in a spinal fusion procedure. The connector of the present invention is particularly useful in revision procedures and/or in procedures where multiple levels of the spine are fused together. The variability and easy connection provided by the connector construct aids in simplifying such procedures.

One aspect of the present invention is an orthopedic rod-to-rod connector including a first connector portion with a first aperture configured to receive at least a portion of a tulip of a screw (e.g., a pedicle or lateral mass screw) and a second connector portion with a second aperture and a third aperture. The third aperture is in communication with a channel for receiving a spinal rod, and the second connector portion is rotatably coupled with the first connector portion. In accordance with the first aspect, an external surface of the tulip may be received within the first aperture.

Other embodiments according to the first aspect may include a first set screw placed through the first aperture and threadably coupled with the tulip. The first set screw may have an extension portion extending through the first and second apertures and may be threadably coupled with a nut. A second set screw may also be threadably coupled with the third aperture and may extend into the channel Tightening of the nut may prevent rotation of the first connector portion with respect to the second connector portion. The second connector portion may include an L-shaped portion defining the channel and a fourth aperture and a depression in communication with the channel. The L-shaped portion may define at least three points of contact on the spinal rod or may define at least three surface contact regions on the spinal rod. The first portion may include an extension received within the second aperture, and the extension may be a circumferential extension.

Another aspect of the present invention is an assembly including a screw portion for engaging a bone, a tulip connected to the screw portion, the tulip having a first channel, a first connector portion with a first aperture receiving at least a portion of an external surface of the tulip, a second connector portion with a second aperture and a third aperture, the third aperture in communication with a second channel, the second connector portion rotatably coupled with the first portion, a first spinal rod disposed within the first channel and a second spinal rod disposed within the second channel. The orientation of the first channel and the second channel may be varied vertically with respect to the screw portion such that the first and second spinal rods disposed in the first and second channel may be co-planar or non-coplanar with a transverse plane of the screw portion.

Embodiments according to this aspect may include a first set screw placed through the first aperture and threadably coupled with the first channel, the first set screw may have an extension portion extending through the first and second apertures and may be threadably coupled with a nut. A second set screw may be threadably coupled with the third aperture and may extend into the second channel that receives the second spinal rod. Tightening of the nut may prevent rotation of the first connector portion with respect to the second connector portion. The connector portion may include an L-shaped portion defining the second channel and a fourth aperture and a depression in communication with the second channel. The L-shaped portion may define at least three points of contact on the spinal rod or may define at least three surface contact regions on the spinal rod. The first connector portion may include an extension received within the second aperture, and that extension may be a circumferential extension.

Yet another aspect of the present invention is an assembly including a screw portion for engaging a bone, a tulip connected to the screw portion, the tulip having a first channel and a first aperture in communication with the first channel, a first connector portion disposed over at least a portion of the tulip, the first connector portion including a second aperture in communication with the first aperture, a second connector portion rotatably coupled with the first portion, the second connector portion having a third aperture in communication with the first and second apertures, a second channel and a fourth aperture in communication with the second channel, a first spinal rod disposed within the first channel, a first set screw threadably coupled within the first aperture and in contact with the first spinal rod, the first set screw including an extension portion extending outside of the first, second and third apertures, a nut threadably coupled to the extension portion, a second spinal rod disposed within the second channel and a second set screw threadably coupled with the fourth aperture and in contact with the second spinal rod.

According to other embodiments of this aspect, the tulip may be polyaxially movable with respect to the screw portion. The tulip may include first and second arms defining the first channel. The first connector portion may include first and second legs that cooperate with the first and second arms. Tightening of the nut may prevent rotation of the first connector portion with respect to the second connector portion. The second connector portion may include an L-shaped member defining the second channel. The L-shaped member may further include a fifth aperture extending orthogonal to the second channel. The second channel may define three points of contact with the second spinal rod or may define at least three surface contact regions on the spinal rod.

Another aspect of the present invention may include an assembly with two rod-to-rod connectors connecting two spinal rods. The rod-to-rod connectors may be attached to parallelly positioned spinal rods such that a first portion of a first spinal rod is disposed in the first channel of the first rod-to-rod connector and a second portion of the spinal rod is disposed in the second channel of the second rod-to-rod connector. In another configuration according to this aspect, a first and second portion of a first spinal rod may be disposed in a first channel of a first rod-to-rod connector and a first channel of a second rod-to-rod connector respectively.

Yet another aspect of the present invention is a surgical method including the steps of providing a first screw including a first spinal rod disposed therein, contacting a first portion of a connector with a portion of the first screw, rotating a second portion of the connector with respect to the first portion and disposing a second spinal rod in a channel of the second portion. The method may also include the further steps of inserting a first set screw through the first connector portion, inserting a second set screw through the second connector portion placing a nut over a portion of the first set screw and tightening the nut to prevent the rotation of the first connector portion with respect to the second connector portion.

BRIEF DESCRIPTION OF THE DRAWINGS

A more complete appreciation of the subject matter of the present invention and of the various advantages thereof can be realized by reference to the following detailed description in which reference is made to the accompanying drawings in which:

FIG. 11A is a perspective view of the connector of FIG. 1 connected with a pedicle screw and two spinal rods in another configuration.

FIG. 11B is a perspective view of the construct of FIG. 11A with two rod-to-rod connectors.

DETAILED DESCRIPTION

In order to develop an appreciation of the principles of the invention, several embodiments as presented in FIGS. 1-10 will be described in the following written specification. The scope of the invention is not intended, however, to be restricted to the embodiments described below. It is also understood that the present invention includes alterations and modifications to the illustrated embodiments and includes further applications of the principles of the invention as would normally occur to one skilled in the art to which this invention belongs.

Figure 1:
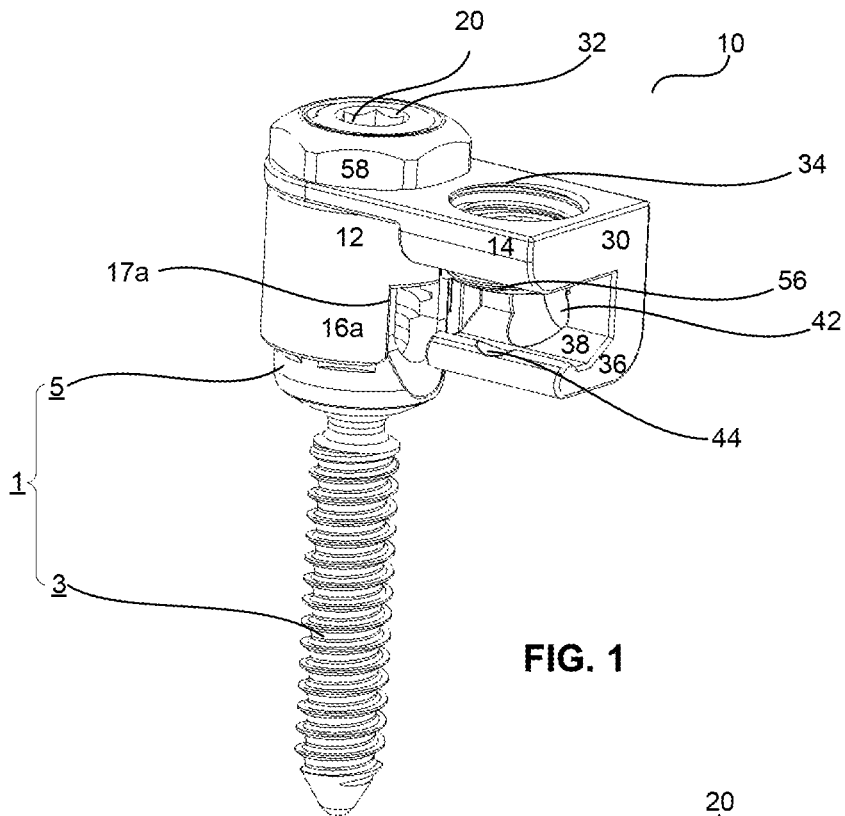
FIG. 1 is a perspective view of a rod-to-rod connector according to one embodiment of the present invention connected with a pedicle screw.
Figure 2:
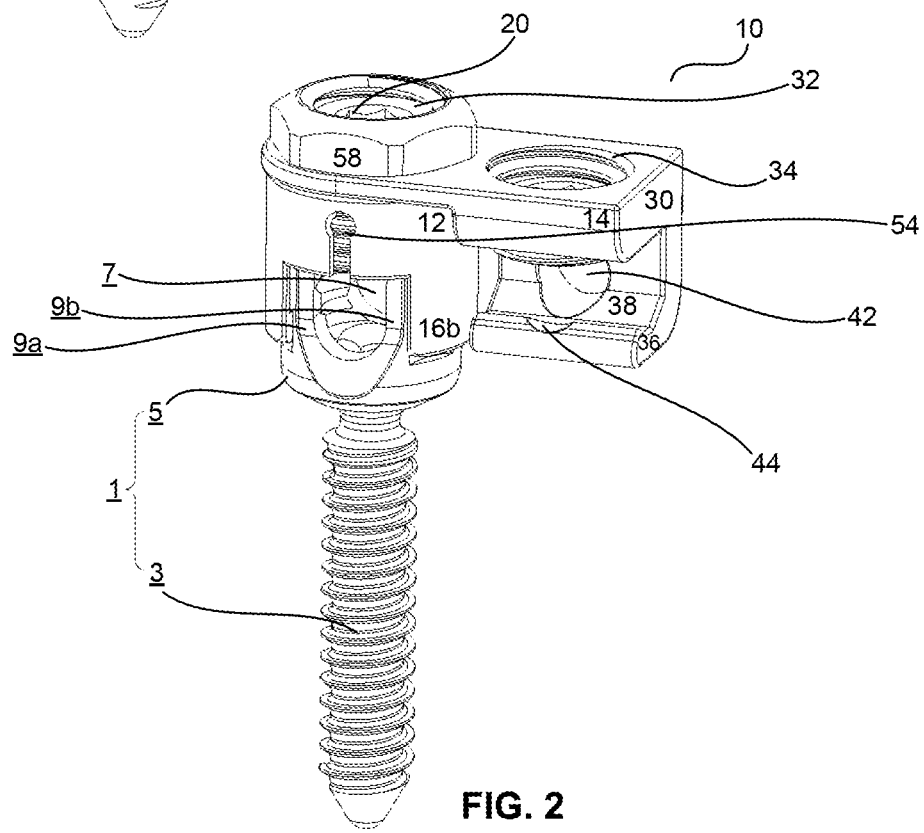
FIG. 2 is another perspective view of the connector of FIG. 1.
Figure 3:
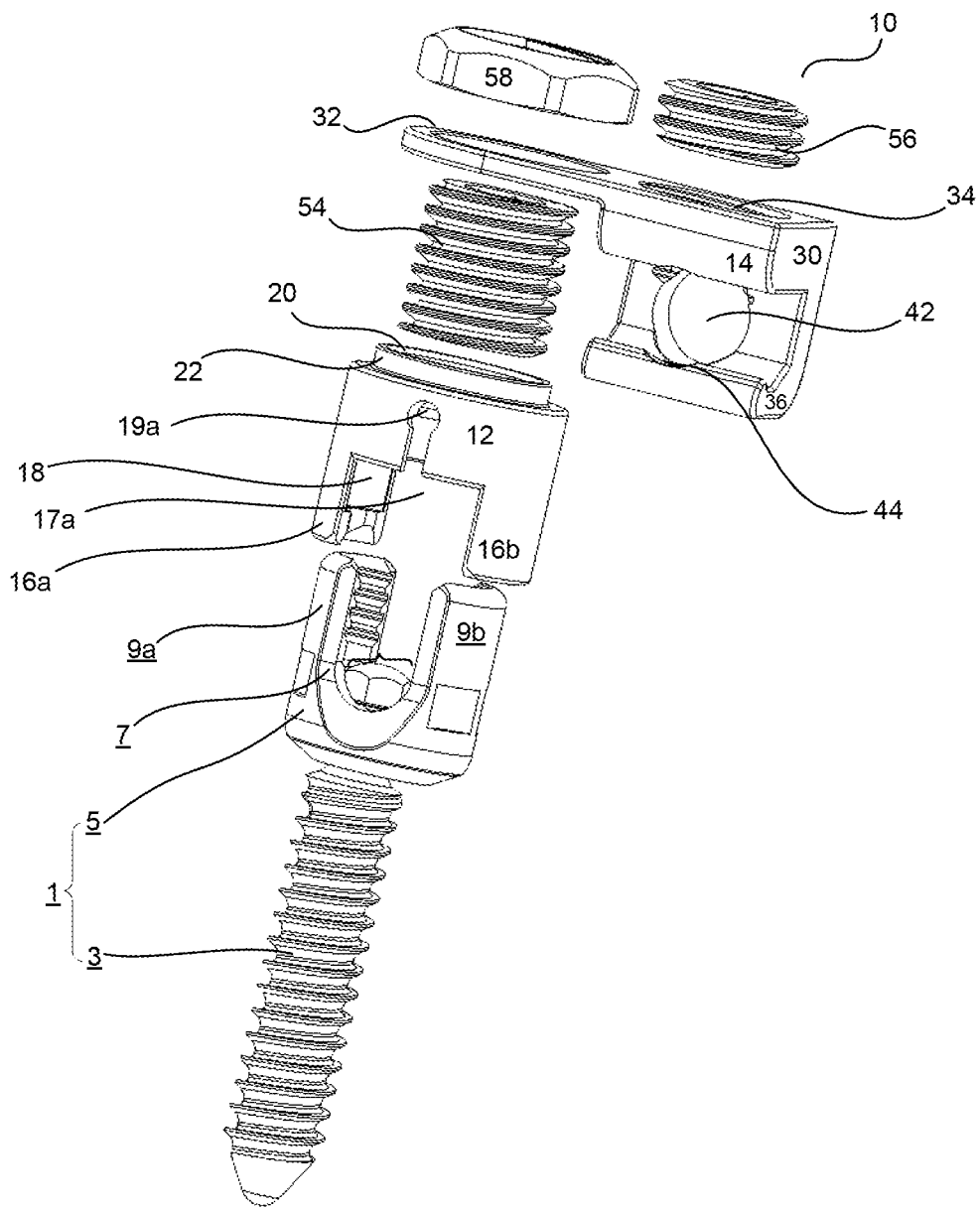
FIG. 3 is an exploded view of the connector of FIG. 1.

As is shown in FIGS. 1 and 2, an orthopedic rod-to-rod connector 10 is disclosed as including two connector portions 12 and 14. The connector portions are rotatably coupled to each other, in the manner discussed more fully below. Connector portion 12 is designed to cooperate with a pedicle screw 1 having a first spinal rod 50 disposed therein, and connector portion 14 is designed to receive a second spinal rod 52. In many cases, this pedicle screw is an already implanted screw, but could be a screw implanted at the time of connector 10. For instance, connector 10 is specifically useful in a revision scenario where a series of pedicle screws (or in the case of the cervical spine, lateral mass screws) linked via a spinal rod are already present in the body, but additional level(s) of fixation are required. However, the connector may also be useful in connecting differently sized spinal rods, where required (e.g., across multiple regions of the spine). Connector 10 is shown in certain of the Figures cooperating with a pedicle screw 1. That device is typical of a standard pedicle or lateral mass screw and includes a screw portion 3 that is polyaxially coupled with a tulip 5, and the tulip also preferably includes a U-shaped channel 7 defined by upstanding threaded arms 9a, 9b. Of course, the present invention can be configured to cooperate with any known pedicle screw, lateral mass screw, hook or the like.

Connector portion 12 includes two legs 16a, 16b which are spaced apart a sufficient distance so as to receive a portion of tulip 5 and define a tulip receiving aperture 18. More particularly, legs 16a, 16b are configured to receive portions of arms 9a, 9b of tulip 5. The legs may include structures capable of cooperating with like structures of tulip 5, for instance, projections that extend into channels or the like. It is also noted that legs 16a, 16b are designed so as to create voids 17a, 17b that do not conflict with a rod extending through channel 7. The small voids 19a, 19b above voids 17a, 17b create space to properly fit in different tulip heads. Connector portion 12 also includes a set screw aperture 20 that is in communication with receiving aperture 18 and channel 7, as well as a circular extension 22 that facilitates the rotatable cooperation with connector portion 14 (best shown in FIG. 4).

Figure 6:
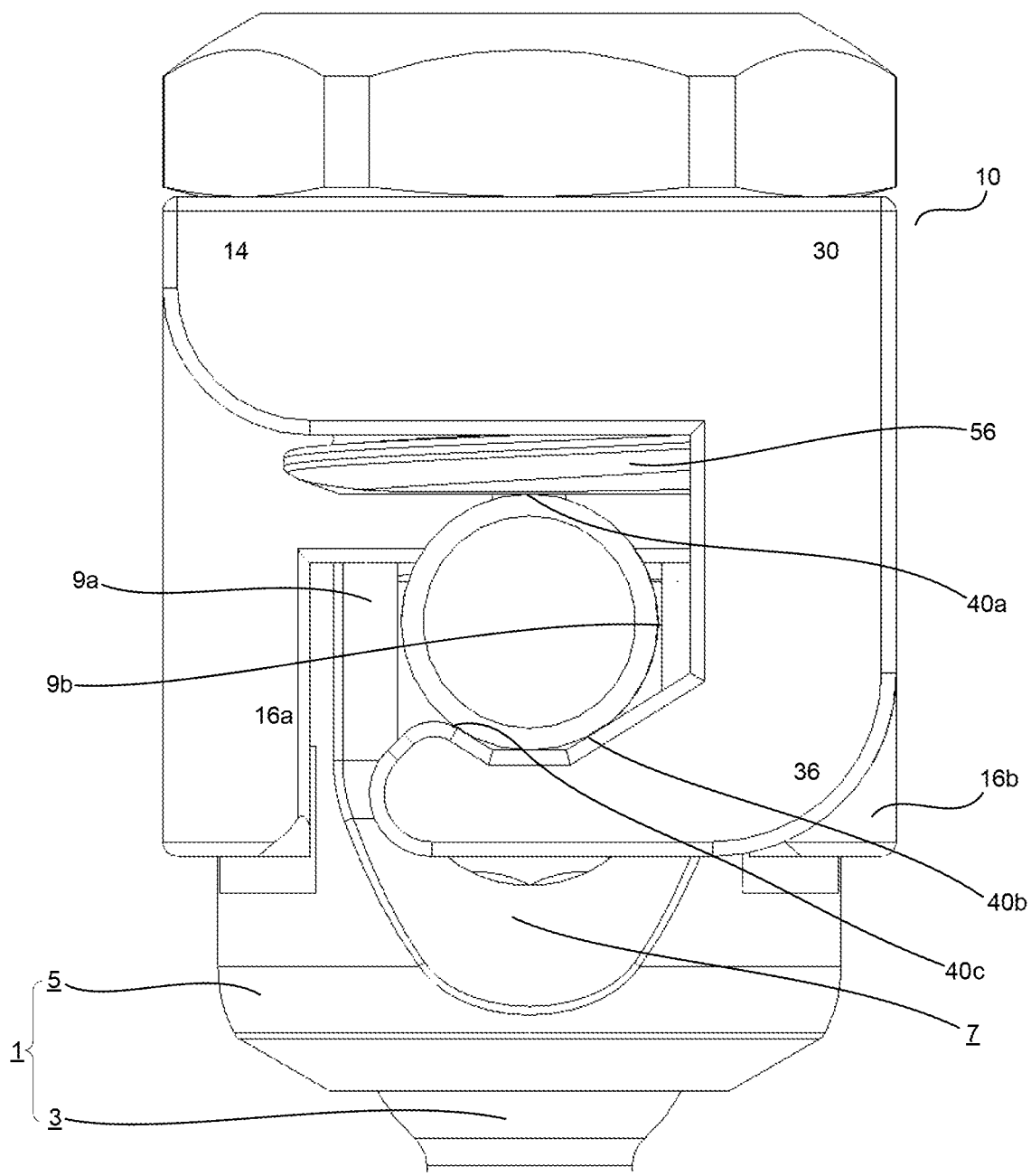
FIG. 6 is an enlarged view of the connector of FIG. 1.

Connector portion 14 includes an upper portion 30 that includes a connection aperture 32 and a set screw aperture 34. Connection aperture 32 is sized and shaped to receive extension 22 in a manner that enables the rotation of connector portions 12, 14 with respect to each other. Connection aperture 32 is in communication with set screw aperture 20, receiving aperture 18 and channel 7. This cooperation will be discussed more fully below. Set screw aperture 34 is threaded and extends over an L-shaped portion 36 that extends below upper portion 30. L-shaped portion 36 defines a channel 38 which is in communication with set screw aperture 34. Again, this will be discussed in more detail below. As is best shown in FIG. 6, L-shaped portion 36 includes surfaces 40a-c that define three points of contact with a rod 52 placed within channel 38. These three major points of intersection 40a, 40b and 40c between the spinal rod and the surface provide for a strong fixation of the rod within the channel. In this manner, a three-point fixation mechanism and a set screw 56 placed through set screw aperture 34 secures the spinal rod 52 in the channel 38. Additionally, L-shaped portion 36 defines a rod aperture 42 (best shown in FIGS. 1 and 2) that extends therethrough and allows for reception of the spinal rod 52 in a direction orthogonal to channel 38. Rod aperture 42 cooperates with a depression 44 formed in surface 40c so as to enable the orthogonal placement of the rod 52. Although orthogonal orientation of the rod with respect to channel 38 is facilitated in the design shown in the Figures, it is to be understood that it is within the scope of the present invention to allow for a different orientation. For instance, rod aperture 42 and depression 44 could be situated to allow for placement of a rod at any angle with respect to channel 38. Both the channel 38 and rod aperture 42 can be sized to accommodate rods of varying diameters such as 3.5 mm, 4.5 mm, 5.5 mm and 6.0 mm in the parallel and orthogonal alignments. In either configuration, the rods connected together via connector 10 can be of varying diameters. The connector 10 therefore, eases the implantation procedure of connecting two rods in a revision scenario or otherwise.

Figure 4:
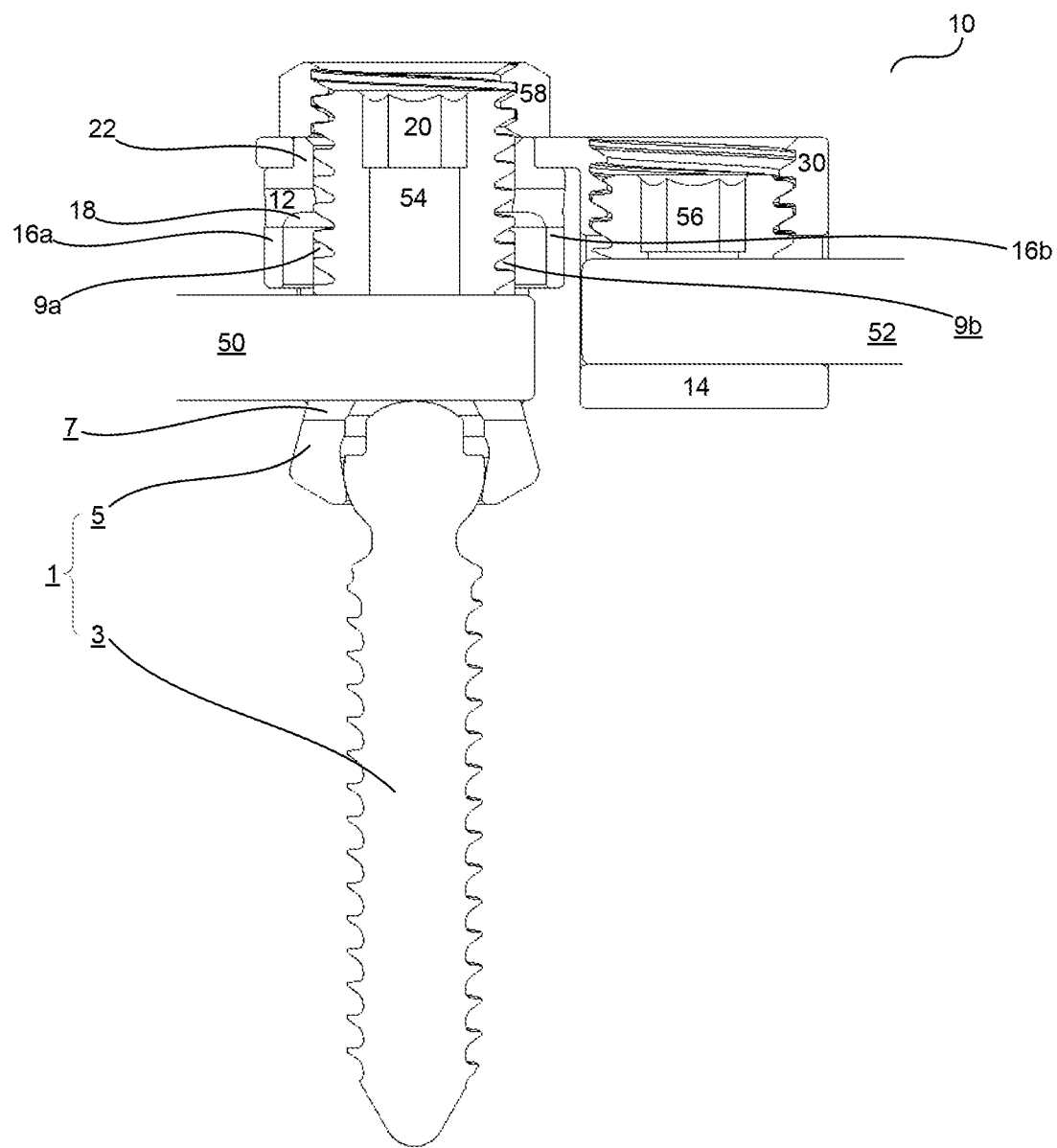
FIG. 4 is a cross-sectional side view of the connector of FIG. 1 connected with a pedicle screw and two spinal rods in a first configuration.
Figure 5:
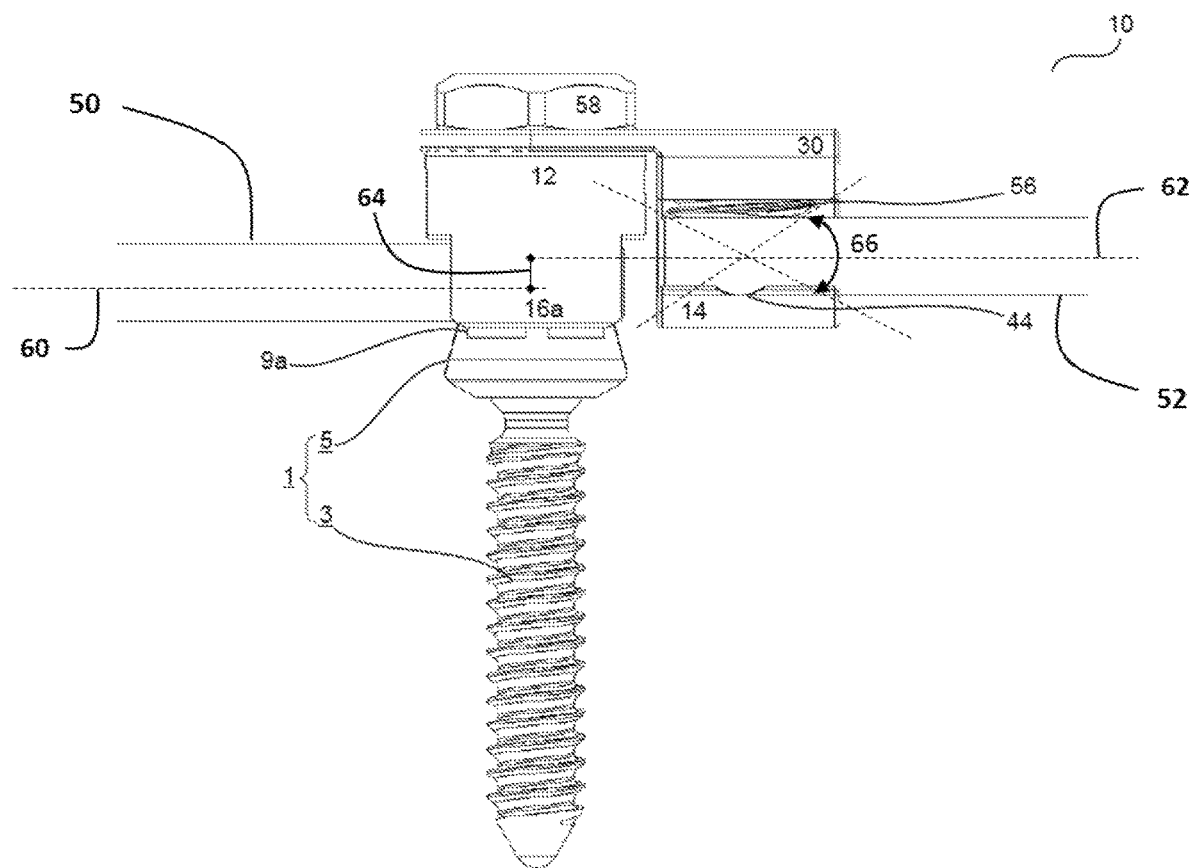
FIG. 5 is a side view of construct of FIG. 4.

In addition to connector 10 and pedicle screw 1, a construct according to the present invention includes set screw 54 and a nut 58. This is best shown in FIGS. 4, 5 and 7-10. Spinal rod 50 is disposed within channel 7 and spinal rod 52 is disposed within channel 38 (either along the channel or orthogonal thereto). Set screw 54 is threaded with threaded arms 9a, 9b of tulip 4 and extends into channel 7 so as to contact spinal rod 50. As in a typical polyaxial pedicle or lateral mass screw design, tightening of set screw 54 bears on rod 50 which in turn prevents movement of screw portion 3 with respect to tulip 5. Set screw 54 also includes an extension portion that extends through apertures 20 and 32 and above upper portion 30 so as to be engageable with nut 58. Tightening of nut 58, not only ensures that connector 10 is held to the pedicle screws, but also prevents rotation of connector portions 12, 14 with respect to each other. As best seen in FIG. 5, a central longitudinal axis 60 of channel 7 and a central longitudinal axis 62 of channel 38 are offset by a distance 64. However, distance 64 can be adjusted by moving channel 38 or channel 7 such that the axes 60 and 62 may be co-planar along a transverse plane with respect to screw portion 3. Furthermore, longitudinal axis 62 of channel 38 can also be vertically varied as shown by arrow 66 to orient spinal rod 52 at any angle with respect to spinal rod 50. Vertical aligment flexibility is intended to allow rod alignment to match curvature of spine.

In one method of use, connector 10 is utilized in connection with the last pedicle (or lateral mass) screw in a previously implanted pedicle (or lateral mass) screw construct when another level or levels of fusion are desired (i.e., a revision procedure). In such a case, the connector is placed over the tulip of the pedicle (or lateral mass) screw, as described above. Given that there is often not a lot of rod overhand from the last pedicle (or lateral mass) screw in the initial assembly, engagement with the original rod is often difficult. Thus, placement of the connector over the pedicle (or lateral mass) screw itself eases performance of the procedure. The connector of the present invention also creates a strong connection point, which improves the overall stability of the resultant construct.

Figure 7:
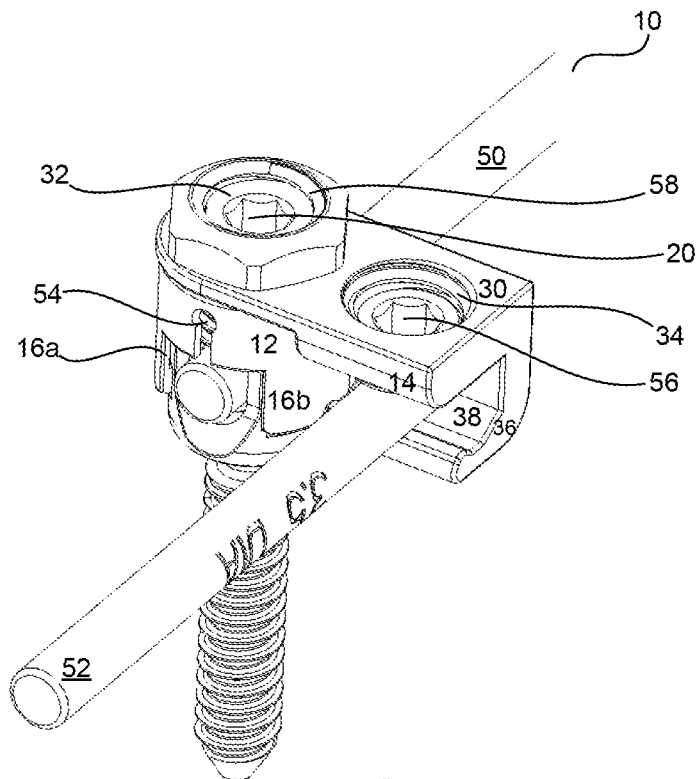
FIG. 7 is a perspective view of the construct of FIG. 4 in a second configuration.
Figure 8:
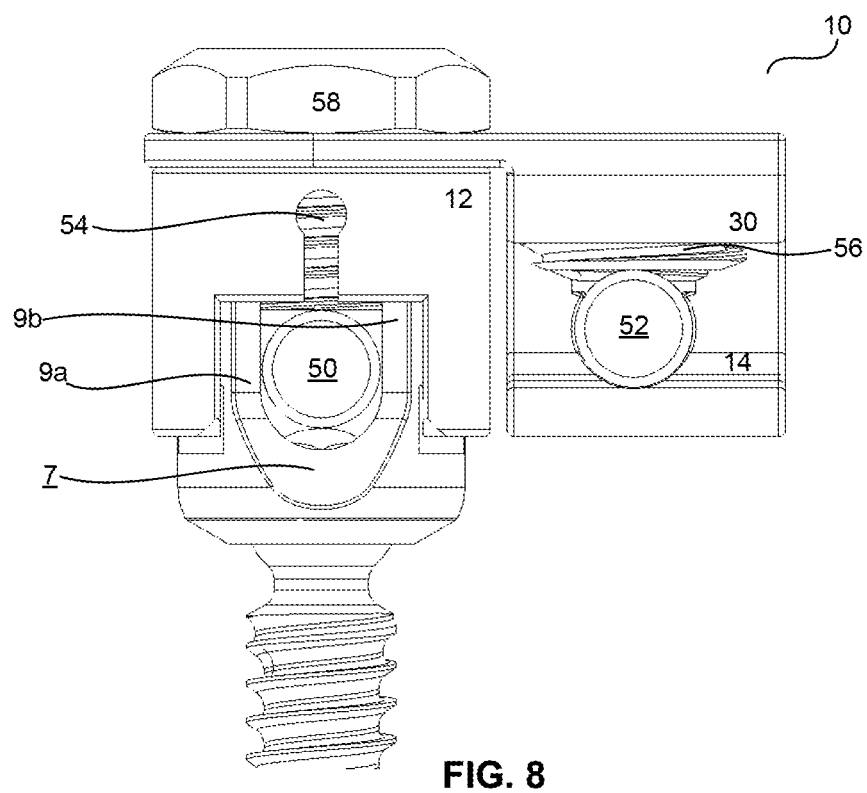
FIG. 8 is side view of the construct of FIG. 7 in the second configuration.
Figure 9:
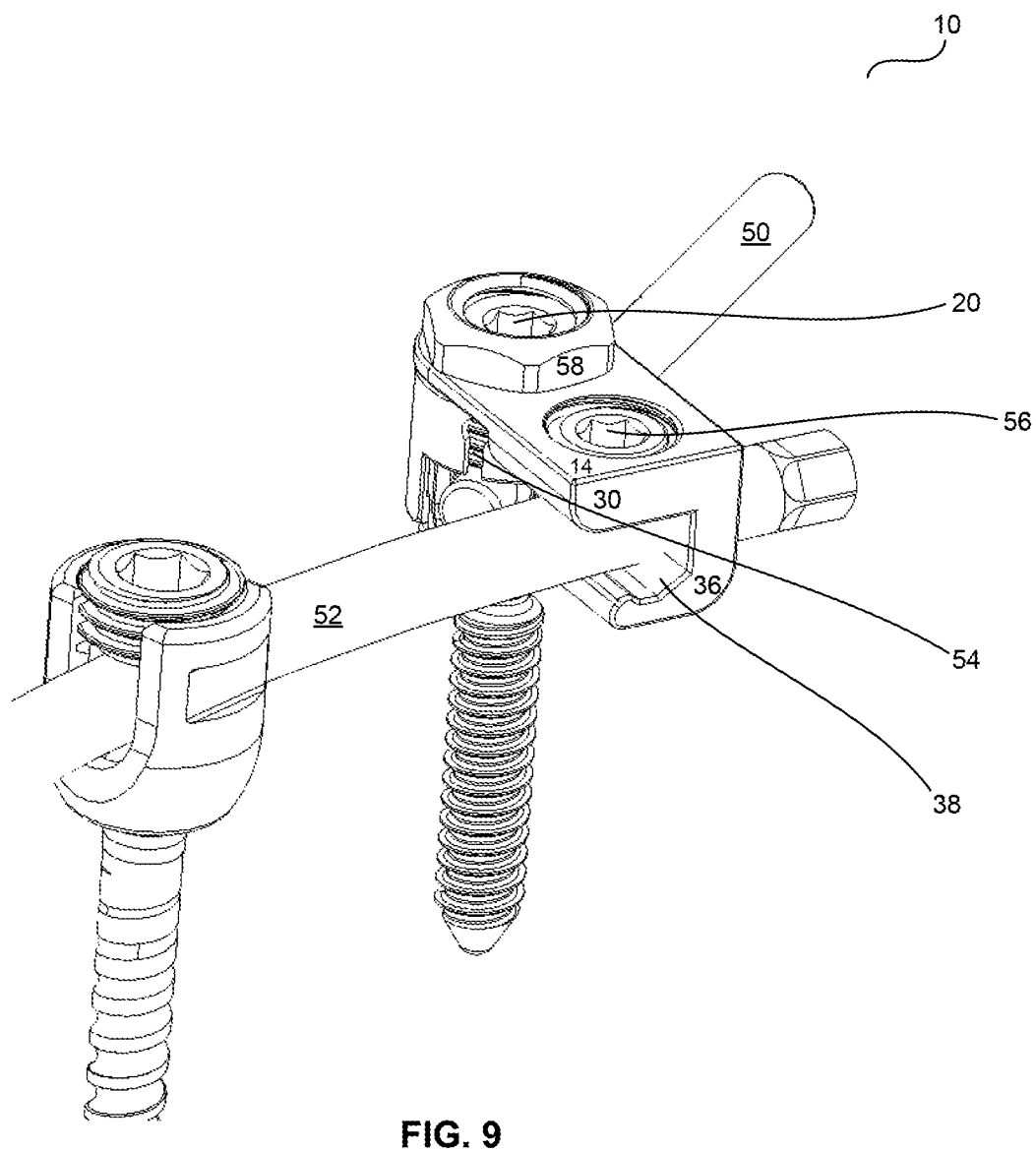
FIG. 9 is a perspective view of the construct of FIG. 4 attached to another pedicle screw.
Figure 10:
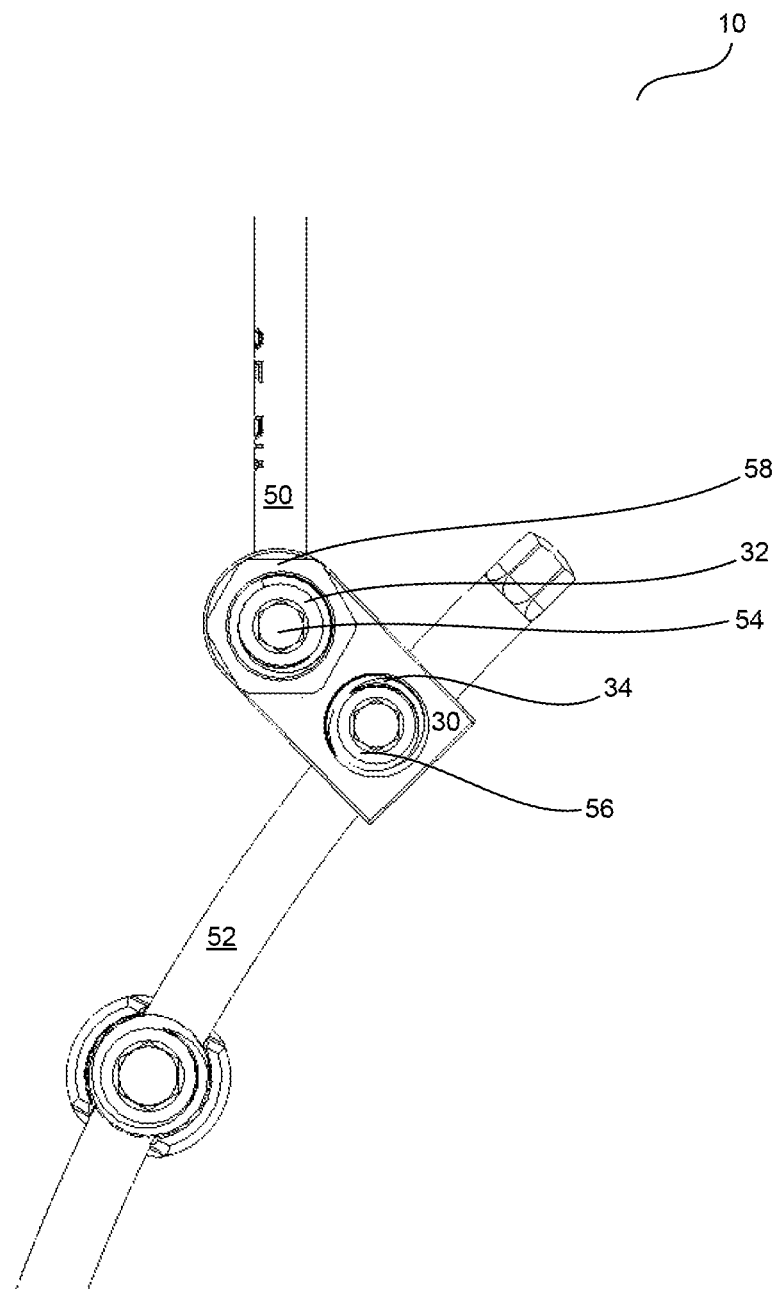
FIG. 10 is a top view of the construct of FIG. 9.

After placement of connector 10, one or more additional pedicle (or lateral mass) screws are then placed in the additional vertebral bodies that are desired to be fused to the previously fused bodies. Connector portion 14 is then rotated with respect to connector portion 12 so as to place it in the most suitable configuration for receiving a second spinal rod for the additional level(s). FIGS. 4 and 5 depict a first configuration in which the already implanted spinal rod and the new spinal rod extend along substantially parallel axes. In this configuration, a rod placed within channel 38 extends along the axis of the channel FIGS. 7 and 8 depict a second configuration in which the spinal rods again extend along substantially parallel axes, but the rod placed through aperture 42 extends orthogonal to the axis of the channel 38. The first and second configurations essentially allow for a different offset distance between the rods. FIGS. 9 and 10 depict a third configuration in which the rods extend at an angle with respect to each other. The rotatable nature of portions 12, 14 allows for this angle to vary, and the flexibility of the placement of a rod within channel 38 allows for further variations in the resultant construct. This is especially beneficial where pedicle (or lateral mass) screws are offset from each other along the spine. Connector 10 enables the rods to be placed even where these offsets may be significant.

Referring now to FIGS. 11A and 11B, there is shown another arrangement of connector 10, wherein connector 10 is located around an interior portion of two spinal rods 50 and 52 away from the ends of these spinal rods. As best shown in FIG. 11B, two connectors 10 and 10' can also be used in a "quad rod" procedure, whereby two rods may be secured across vertebrae. A quad rod technique generally employs four rods instead of two rods across the vertebrae. A second rod is added to the main rod on each side of the spinous process and connected by rod-to-rod connectors to increase overall rigidity of the fixation assembly. As shown here, a second rod 52 may be added to a main rod 50 on each side of the spinous process and connected by two rod-to-rod connectors 10 and 10' to perform a quad rod procedure. The rod-to-rod connectors may be oriented in opposite directions such that spinal rod 50 may be disposed in the first channel of connector 10 and the second channel 38' of connector 10' as shown in FIG. 11B. This allows for anchoring at least one screw portion 3 to each spinal rod. Other configurations may have the rod-to-rod connectors oriented in the same direction wherein spinal rod 52 may be disposed in the first channel of the first rod connector and the first channel of the second rod connector. While two rod-to-rod connectors are shown in FIG. 11B, other embodiments may have multiple rod-to-rod connectors attached to two or more spinal rods. Further connector 10 may be used in conjunction with spinal fixation assemblies comprising spinal rod loops, spinal rod connectors and spinal rod reinforcers disclosed in U.S. Provisional Application No. 62/362,690, the disclosure of which is hereby incorporated by reference herein.

The connector of the present invention is also useful in situations where vertebral bodies across different regions of the spine are being fused by a rod and screw construct. Typically, such constructs involve the use of tapering spinal rods that allow for placement of the rod in pedicle screws sized for the different regions (or in the case of the cervical spine, within lateral mass screws). For instance, a construct extending between the thoracic and lumbar regions of the spine will include a rod with a smaller diameter end for reception within the pedicle screws placed in the thoracic region and a larger diameter end for reception within the pedicle screws placed in the lumbar region. A problem that is often faced in such constructs is that the size and/or orientation of the vertebral bodies requires a level to be skipped. Such region spanning constructs have also been addressed by utilizing two differently sized rods that are connected via a different type of rod-to-rod connector that again often requires the skipping of a level. Use of the connector of the present invention negates the need for such level skipping. For instance, in the foregoing situations, connector 10 can be placed over a pedicle screw (or a lateral mass screw) in the construct and engaged with one of the differently sized rods. Thus, every level can be provided with a pedicle screw and none need to be skipped.

The various components of the present invention can be constructed of many different materials, preferably materials suitable for implantation in the body. Such components must also be able to withstand the forces typically present in a spinal fusion situation. For instance, it is contemplated to form the various portions of a metallic material, such as stainless steel or titanium. Of course, other materials may be utilized and different portions of the devices disclosed herein can be constructed of different materials from each other. It is also contemplated to provide connectors of varying sizes/configurations for use in connection with differently sized or configured pedicle (or lateral mass) screws and rods. The various connectors may be provided in a kit along with corresponding set screws, rods, etc. Of course, tools suitable for implantation and fixation of the connectors according to the present invention may also be provided. These may include drivers, clamps and other tools necessary to enable the proper application and use of the connectors.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopedic rod-to-rod connector comprising:
    a first connector portion with a first aperture configured to receive at least a portion of a tulip of a screw,
    a second connector portion with a second aperture and a third aperture, the third aperture in communication with a channel, wherein the channel is a through bore extending along a first direction for receiving a first spinal rod, wherein the second connector portion is rotatably coupled with the first connector portion, the second connector portion including a fourth aperture in communication with the channel, the fourth aperture forming a through bore through the second connector portion and configured to receive a second spinal rod such that the second spinal rod is transverse to the first direction; and
    a first set screw placed through the first aperture and threadably coupled with the tulip, the first set screw having an extension portion extending through the first and second apertures and threadably coupled with a nut.

2. The connector of claim 1, wherein at least a portion of an external surface of the tulip is received within the first aperture.

3. The connector of claim 1, further comprising a second set screw threadably coupled with the third aperture and extending into the channel.

4. The connector of claim 1, wherein tightening of the nut prevents rotation of the first connector portion with respect to the second connector portion.

5. The connector of claim 1, wherein the second connector portion includes an L-shaped portion defining the channel and a depression in communication with the channel.

6. The connector of claim 5, wherein the L-shaped portion defines at least 3 points of contact on the first spinal rod.

7. The connector of claim 1, wherein the first connector portion includes an extension received within the second aperture.

8. The connector of claim 7, wherein the extension is a circumferential extension.

9. An assembly comprising:
    a screw portion for engaging a bone;
    a tulip connected to the screw portion, the tulip having a first channel;
    a first connector portion with a first aperture receiving at least a portion of an external surface of the tulip;
    a second connector portion with a second aperture and a third aperture, the third aperture in communication with a second channel, wherein the second channel is a through bore extending along a first direction, the second connector portion rotatably coupled with the first connector portion, the second connector portion including a fourth aperture in communication with the second channel, the fourth aperture forming a through bore through the second connector portion and configured to receive a third spinal rod such that the third spinal rod is transverse to the first direction;
    a first spinal rod disposed within the first channel;
    a second spinal rod disposed within the second channel, and
    a first set screw placed through the first aperture and threadably coupled with the first channel, the first set screw having an extension portion extending through the first and second apertures and threadably coupled with a nut.

10. The assembly of claim 9, further comprising a second set screw threadably coupled with the third aperture and extending into the second channel that receives the second spinal rod.

11. The assembly of claim 9, wherein a tightening of the nut prevents the rotation of the first connector portion with respect to the second connector portion.

12. The assembly of claim 9, wherein the second connector portion includes an L-shaped portion defining the second channel and a depression in communication with the second channel.

13. The assembly of claim 12, wherein the L-shaped portion defines at least 3 points of contact on the second spinal rod.

14. The assembly of claim 9, wherein the first connector portion includes an extension received within the second aperture.

15. The assembly of claim 9, wherein the tulip includes first and second arms defining the first channel.

16. The assembly of claim 15, wherein the first connector portion includes first and second legs that cooperate with the first and second arms.

17. The assembly of claim 9, wherein the tulip is polyaxially movable with respect to the screw portion.

* * * * *